United States Patent [19]
Hill et al.

[11] Patent Number: 5,382,529
[45] Date of Patent: Jan. 17, 1995

[54] ASSAY FOR DIBROMONITRILOPROPIONAMIDE

[75] Inventors: Martyn W. Hill, Saffron Walden, Great Britain; Dennis F. Sharman, Oststeiermark, Austria

[73] Assignee: CTS Biocides Ltd., Cambridge, Great Britain

[21] Appl. No.: 90,182

[22] PCT Filed: Nov. 15, 1991

[86] PCT No.: PCT/GB91/02015
§ 371 Date: Jul. 23, 1993
§ 102(e) Date: Jul. 23, 1993

[87] PCT Pub. No.: WO92/09890
PCT Pub. Date: Jun. 11, 1992

[30] Foreign Application Priority Data
Nov. 23, 1990 [GB] United Kingdom ............... 9025516

[51] Int. Cl.⁶ ............................................ G01N 33/15
[52] U.S. Cl. ................................... 436/109; 436/106; 436/166; 422/61
[58] Field of Search ............... 436/106, 109, 131, 166; 422/61

[56] References Cited
U.S. PATENT DOCUMENTS
3,519,711 7/1970 Svigals ........................... 424/148
4,761,427 8/1988 Segall et al.

FOREIGN PATENT DOCUMENTS
0016578 10/1980 European Pat. Off.
245945 11/1987 European Pat. Off.
3306956 9/1983 Germany.
59-42450 3/1984 Japan ........................... 436/131
873121 10/1981 U.S.S.R.

OTHER PUBLICATIONS
R. I. Botto et al. *Anal. Chem.*, 1981, 53, 2375–2376.
S. Honda et al. *Anal. Chim. Acta* 1983, 149, 297–303.

Primary Examiner—James C. Housel
Assistant Examiner—Arlen Soderquist
Attorney, Agent, or Firm—Oliff & Berridge

[57] ABSTRACT

A method of testing for the presence of dibromonitrilopropionamide in a sample, which comprises adding to the sample, under alkaline conditions and in the presence of magnesium ions, a phenolic or anilinic compound that generates a colour; and observing the resultant colour. The appropriate reagents may be formulated as a kit, e.g. using pyrocatechol as the phenolic compound.

7 Claims, No Drawings

ASSAY FOR DIBROMONITRILOPROPIONAMIDE

FIELD OF THE INVENTION

This invention relates to an assay for the compound $NC-C(Br)_2-CONH_2$, i.e. dibromonitrilopropionamide (DBNPA).

BACKGROUND OF THE INVENTION

DBNPA is a biocide that is used in cooling towers, in order to control organisms such as Legionella, in papermaking, and in other aqueous environments. An object behind the invention is to monitor the level of such compounds in the water.

SUMMARY OF THE INVENTION

According to the present invention, a method of testing for the presence of DBNPA in a sample comprises adding to the sample, under alkaline conditions and in the presence of a magnesium compound, a phenolic or anilinic compound that generates a colour; and observing the resultant colour.

The invention is based on the discovery that there are many phenolic and anilinic compounds which can react with DBNPA, to generate a coloured species, in the presence of magnesium ions. The novel method is both simple and effective. A kit of the essential components can be provided.

DESCRIPTION OF THE INVENTION

The reaction is preferably conducted at a pH of 8.5 to 10, e.g. about 9. For this purpose, a buffer such as an alkali metal tetraborate (e.g. borax), Tris.HCl or Tris-glycine.HCl can be used.

The magnesium ions can be provided in the form of any Mg compound that catalyses the reaction. $MgCO_3$, as present in hard water can be used, as can $MgCl_2$, $MgSO_4$, $Mg(NO_3)_2$ and other Mg salts. Calcium, sodium, potassium and aluminium ions apparently do not catalyse the reaction.

The assay may be affected by the presence of iron (III) or iron (II). If present, iron ions are therefore preferably removed, e.g. using a cation-exchange resin.

The phenolic or anilinic compound can be chosen, depending on the conditions, by anyone skilled in the art. It is preferably pyrocatechol, although it may be any analogous compound, e.g. of the 1,4-benzenediol/-benzenediamine/aminophenol or, preferably, 1,2-benzenediol/benzenediamine/aminophenol-type. Colours given by certain such compounds are tabulated below:

| Compound | Colour |
| --- | --- |
| pyrocatechol | distinctive violet (turns yellow in acid) |
| hydroquinone | relatively evanescent blue-green |
| (3,4-dihydroxyphenyl)acetic acid | violet |
| (3,4-dihydroxyphenyl)acetamide | red-purple |
| [2-(3,4-dihydroxyphenyl)ethyl]-trimethylammonium chloride | violet |
| (3,4-dihydroxyphenyl)glycol | violet |
| 2-(3,4-dihydroxyphenyl)ethanol | violet |
| 3-methylcatechol | deep purple |
| 4-methylcatechol | blue-red |
| o-phenylenediamine | red |
| p-phenylenediamine | red-orange | m-Phenylenediamine gives no colour, and neither does phenol, but the use of such compounds is included within the scope of this invention; a colour can be generated by the addition of an oxidising agent such as periodate. Guaiacol gives an orange colour, and isohomovanillic acid faint purple, in the presence of borax. The colour is likely to be pH-dependent, but the optimum pH can be determined simply.

In use of the method according to the invention, the colour that is generated is preferably compared with a blank of the phenolic or anilinic compound. The colour can be measured by any suitable means.

The following Examples illustrate the invention.

EXAMPLE 1

To aqueous DBNPA was added 10% v/v of Tris-HCl buffer, pH 9.1, containing a catalytic amount of $MgCl_2$. Pyrocatechol was added in aqueous form, to a concentration of 50 $\mu$g/ml. A violet colour was allowed to develop over 5 minutes, and was read at 537 nm. The colour turned yellow in acid. It also acted as an oxidation-reduction indicator, and was decolorised by $SnCl_2$ and $K_3Fe(CN)_6$. The reading allowed quantification of the amount of DBNPA, by comparison with a pyrocatechol-containing blank.

EXAMPLE 2

The following steps were conducted:
1. To a 3 ml water sample containing DBNPA, add 25 $\mu$l of 0.1 M $MgCl_2$. Mix thoroughly.
2. Add 200 $\mu$l of 0.2 M Tris buffer. Mix.
3. Add 150 $\mu$l 1.5 mg/ml 0.001M catechol. Mix.
4. After 3 minutes, read the optical density at 550 nm.

EXAMPLE 3

The following steps were carried out:
1. Dilute 1.5 ml of sample to 3 ml with RO water.
2. Pass the diluted sample through a column containing Dowex 50W-X8 cationic resin in the lithium form.
3. Add 25 $\mu$l of 0.1M magnesium chloride to the column eluent. Mix.
4. Add 200 $\mu$l of a Tris/hydrochloric acid buffer. Mix.
5. Add 150 $\mu$l of a catechol solution. Mix.
6. After 3 minutes, read the optical density at 550 nm.

We claim:

1. A method of testing for the presence of dibromonitrilopropionamide in a sample, which comprises adding to the sample, an alkaline buffer, magnesium ions, and a phenolic or anilinic compound for generating a color; and determining the resultant color.

2. A method according to claim 1, in which the phenolic or anilinic compound is pyrocatechol.

3. A method according to claim 1, which is conducted at a pH of 8.5 to 10.

4. A method according to claim 1, which is conducted in the absence of iron ions.

5. A method according to claim 4, which additionally comprises the prior step of removing iron ions.

6. A kit for determining dibromonitriloproionamide in a sample comprising containers containing respectively a buffer for maintaining a pH of 8.5-10; and a phenolic or anilinic compound selected from the group consisting of pyrocatechol, hydroquinone, (3, 4-dihydroxyphenyl) acetic acid, (3, 4-dihydroxyphenyl) acetamide, [2- (3, 4-dihydroxyphenyl) ethyl]trimethylammonium chloride, (3,4-dihydroxyphenyl)glycol, 2-(3,4-dihydroxyphenyl)ethanol, 3-methylcatechol, 4-methylcatechol, o-phenylenediamine, and p-phenylenediamine; said kit further comprising magnesium ions in at least one container.

7. A kit according to claim 6, in which the phenolic or anilinic compound is pyrocatechol.

* * * * *